United States Patent [19]

Nishigaki et al.

[11] Patent Number: 4,879,992
[45] Date of Patent: Nov. 14, 1989

[54] RIGID ELECTRONIC ENDOSCOPE

[75] Inventors: Shinichi Nishigaki, Tokyo; Takeaki Nakamura; Jun Yoshinaga, both of Hino; Masahide Kanno, Hachioji; Hisao Yabe, Hachioji; Takeshi Yokoi, Hachioji; Kazuhiko Oozeki, Hachioji; Yoshikazu Tojo, Hachioji; Hiromasa Suzuki, Akishima, all of Japan

[73] Assignee: Olympus Optical Co., Ltd., Tokyo, Japan

[21] Appl. No.: 187,199

[22] Filed: Apr. 26, 1988

[30] Foreign Application Priority Data

Apr. 27, 1987 [JP] Japan .................................. 62-104032

[51] Int. Cl.⁴ ............................................... A61B 1/04
[52] U.S. Cl. ............................................ 128/6; 358/98
[58] Field of Search ................................. 128/6; 358/98

[56] References Cited

U.S. PATENT DOCUMENTS

| 4,527,552 | 7/1985 | Hattori | 128/6 |
| 4,625,714 | 12/1986 | Toyota et al. | 128/6 |
| 4,631,582 | 12/1986 | Nagasaki et al. | 128/6 |
| 4,779,130 | 10/1988 | Yabe | 128/6 |

Primary Examiner—Leo P. Picard
Attorney, Agent, or Firm—Armstrong, Nikaido, Marmelstein, Kubovcik & Murray

[57] ABSTRACT

This rigid electronic endoscope has an endoscope having an elongate insertable part connected to the front part of an operating part which is also a holding part on the base side and formed of a solid state imaging device which can output an electric signal by electrically converting an object image in this insertable part and a conductive shielding member sheathing this insertable part. The electric signal obtained by this endoscope is input into a signal processing circuit. The ground terminal of this signal processing circuit is electrically connected to the above mentioned shielding member and is isolated from a ground terminal on the external current source side.

4 Claims, 3 Drawing Sheets

RIGID ELECTRONIC ENDOSCOPE

FIELD OF THE INVENTION

This invention relates to a rigid electronic endoscope forming a shielding means.

BACKGROUND OF THE INVENTION

Recently, there has come to be extensively used an endoscope whereby an affected part or the like within a body cavity can be observed or diagnosed by inserting an elongate insertable part into the body cavity or a curing treatment can be made by using treating tools as required.

Also, there is recently practiced an electronic endoscope (mentioned also as an electronic scope) whereby an image is formed on an imaging surface of a solid state imaging device by objective lenses without using an image guide formed of a fiber bundle and a video signal photoelectrically converted by this solid state imaging device is transmitted to a signal processing means and is color-displayed by a monitor.

Now, in the above mentioned electronic endoscope, when such electric device as a high frequency treating tool is used, a high frequency noise will be output, will be therefore likely to be mixed in an output video signal of the solid state imaging device, will appear on the displaying picture surface and will remarkably reduce the picture quality of the endoscope picture imaged by the solid state imaging device and, in fact, an observation or diagnosis will be no longer able to be made.

In the publication of a U.S. Pat. No. 4,607,621, for the protection from such high frequency noise, there is disclosed a technique wherein an imaging device and video and signal transmitting electric wires are contained in a conductive shield which is electrically connected to a chassis of a video processor and further this chassis is connected to an RF earthing point of a high frequency current source apparatus.

Now, in this technique, as the chasis and shield are connected with each other, a leaking electric current will be likely to flow out of the shield to cause a very dangerous state.

OBJECT AND SUMMARY OF THE INVENTION

An object of the present invention is to provide a rigid electronic endoscope having a sufficient shielding function against high frequency noises and capable of obtaining an endoscope picture of a required picture quality.

The rigid electronic endoscope of the present invention is provided with an endoscope having a solid state imaging device as an imaging means and a controlling apparatus containing a signal processing circuit for the electric signal output from this endoscope. A conductive shielding member to externally shield this endoscope is connected to the ground terminal of the above mentioned signal processing circuit to form a shielding means.

The other features and advantages of the invention will become apparent enough with the following explanation.

Figure 1:
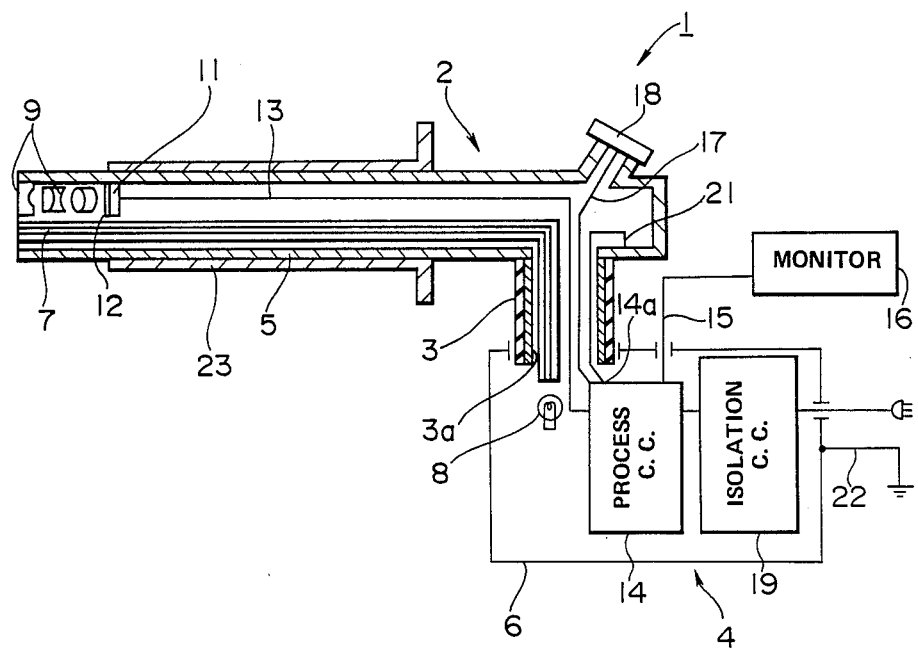
FIG. 1 relates to the first embodiment of the present invention and a formation view of a rigid electronic endoscope.

Fog. 4 relates to the fourth embodiment of the present invention and is a formation view of a rigid electronic endoscope.

DETAILED DESCRIPTION OF PREFERRED EMBODIMENTS

The present invention shall be concretely explained in the following with reference to the drawings.

A rigid electronic endoscope apparatus 1 of the first embodiment is formed of a rigid electronic endoscope body 2 and an endoscope controlling apparatus 4 connected to this (rigid electronic) endoscope body 2 through a connecting tube 3.

The above mentioned endoscope body 2 is covered with a metallic sheath tube 5 made of a copper alloy or Ni-Cr plated stainless steel and is connected with a flexible connecting tube 3 extended out of the side part of the rear end side of this sheath tube 5.

The above mentioned connecting tube 3 has a shielding net tube 3a or the like made by knitting metal wires or the like to be net-like. This shielding net tube 3a is electrically connected to the sheath tube 5 but is electrically isolated from a sheathing metal part 6 of the controlling apparatus 4.

The above mentioned sheath tube 5 is formed to be like a thin circular tube through which a light guide 7 formed of a fiber bundle is inserted. This light guide 7 is further inserted through the connecting tube 3 and is fed with a white illuminating light from a light source lamp 8 of the controlling apparatus 4. The illuminating light radiated onto the entrance end surface on the base side of this light guide 7 is transmitted by the light guide 7 and is radiated toward an object to be imaged from the tip surface of this light guide. The image of the illuminated object is formed by an objective lens system 9 arranged adjacently to the tip part of the light guide 7 on a CCD (charge coupled device) 11 having the imaging surface arranged in the focal plane of this objective lens system 9. This CCD 11 photoelectrically converts the optical image formed on the imaging surface and outputs a photoelectrically converted video (picture) signal by the application of a CCD driving signal output from a driving circuit not illustrated, for example, within the controlling apparatus. By the way, a color mosaic filter 12 in which red, green and blue color transmitting filters are arranged in the form of a mosaic by the pixel unit or the like is arranged on the imaging surface of the CCD 11. Therefore, the picture signal output from the CCD 11 becomes a color picture signal. This picture signal is transmitted through the signal cable 13 and is input into a video process circuit 14 within the controlling apparatus 4. By this video process circuit 14, the input picture signal is treated to be separated in colors, is converted to an NTSC compound video signal or RGB3-primary color signals, is output in an observing monitor 16 through a video cable 15 and is output also in a flat plate-like display 18 fitted near the base side end of the endoscope body 2 through a video cable 17 inserted through the endoscope body 2 to color-display the object image by the monitor 16 and (flat plate-like) display 18.

The above mentioned video process circuit 14 is to be fed with an electric power from a commercial current source as electrically isolated through an isolation circuit 19.

Now, the ground (GND) terminal 14a of the above mentioned video process circuit 14 is connected with one place, for example, on the rear end side of the sheath tube 5 through an earthing line 21 and the potential of the sheath tube 5 is held on the GND level of the video process circuit 14.

By the way, as the connecting tube 3 is electrically connected with the sheath tube 5 by the shielding net tube 3a, this shielding net tube 3a is held on the same level as of the GND of the video process circuit 14.

On the other hand, the sheathing metal part 6 is connected to the GND of a commercial current source, that is, to the earth by an earthing line 22. The GND terminal 14a of the video process circuit 14 is in a floating state from the GND of this commercial current source.

By the way, the sheath tube 5 as fitted in a jacket tube 23 can be inserted into a body cavity or the like. This jacket tube 23 is made of a stainless steel or Ni-Cr plated copper alloy the same as in the sheath tube 5 and is in mechanical and electrical contact with the sheath tube 5.

In this first embodiment, it is a feature that the metallic sheath tube 5 forming the sheathing member of the endoscope body 2 is connected with the GND terminal 14a of the video process circuit 14 into which the video signal of the CCD 11 shielded with the sheath tube 5 and this GND terminal 14a is in a floating state with the GND terminal on the external current source side to form a shielding means.

By the way, the forceps channel not illustrated is made of a metal or is covered with a metal so that, in case a high frequency treating tool is used, the radiation on the periphery may be reduced, is electrically connected with the sheath tube 5 and is held at the same potential as of this sheath tube 5.

According to the thus formed first embodiment, for example, in case a high frequency treating tool is used by an electric power fed from as commercial current source, the high frequency waves will be prevented by the sheath tube 5 of the like from being mixed as noises into the output signal cable 13 of CCD 11. Also, the high frequency output circuit side outputting the electric power for the high frequency treating tool and the video process circuit 14 side are isolated from each other by the isolation circuit 19, the GND of the video process circuit 14 is in a floating state against the GND (substantially equal to the earthing of the commercial current source) of the high frequency output circuit and therefore, even if a high frequency noise mixes in the signal cable 13, this high frequency noise will be substantially of the same potential as of the GND of the video process circuit 14 (as different from the case that the GND of the video process circuit 14 must be isolated from the GND of the high frequency output circuit) and will not substantially influence the signal.

Therefore, the deterioration of S/N can be made small and the reduction of the picture quality can be made small enough.

Figure 2:
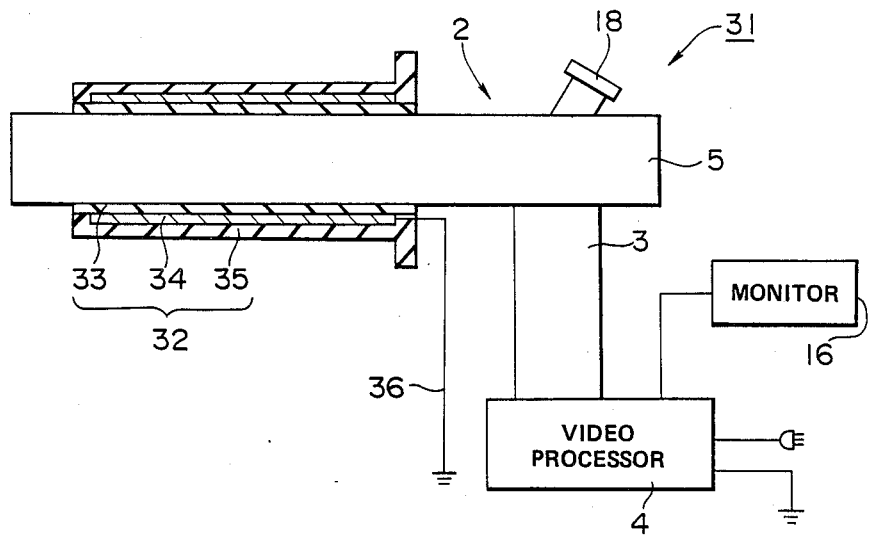
FIG. 2 relates to the second embodiment of the present invention and is a formation view of a rigid electronic endoscope.

FIG. 2 shows the second embodiment, of the present invention. In a rigid electronic endoscope apparatus 31 of this second embodiment, the jacket tube 23 in the electronic endoscope apparatus 1 shown in FIG. 1 is made a jacket tube 32 of a structure of three layers.

That is to say, the jacket tube 32 consists of three layers of an inner layer 33, middle layer 34 and outer layer 35. Each of the inner layer 33 and outer layer 35 is formed of an insulating member. The middle layer 34 is formed of such conductive member as of a metal and is earthed through an earthing line 36.

In this second embodiment, as the inner layer 33 is formed of an insulating member, the sheath tube 5 of the endoscope body 2 will not be of the earthing potential and this body 2 will be held in a floating state.

Also, as the outer layer 35 is formed of an insulating member, in the case of the use within a body cavity, the patient himself will be able not to be of the earthing potential.

The others are of the same formation as of the above mentioned first embodiment. The same reference numerals are attached respectively to the same members.

In this second embodiment, as the middle layer 34 of the jacket tube 32 is earthed, this middle layer 34 will further have a shielding function against external noises and noises will be able to be well prevented from mixing into the CCD output signal.

Figure 3:
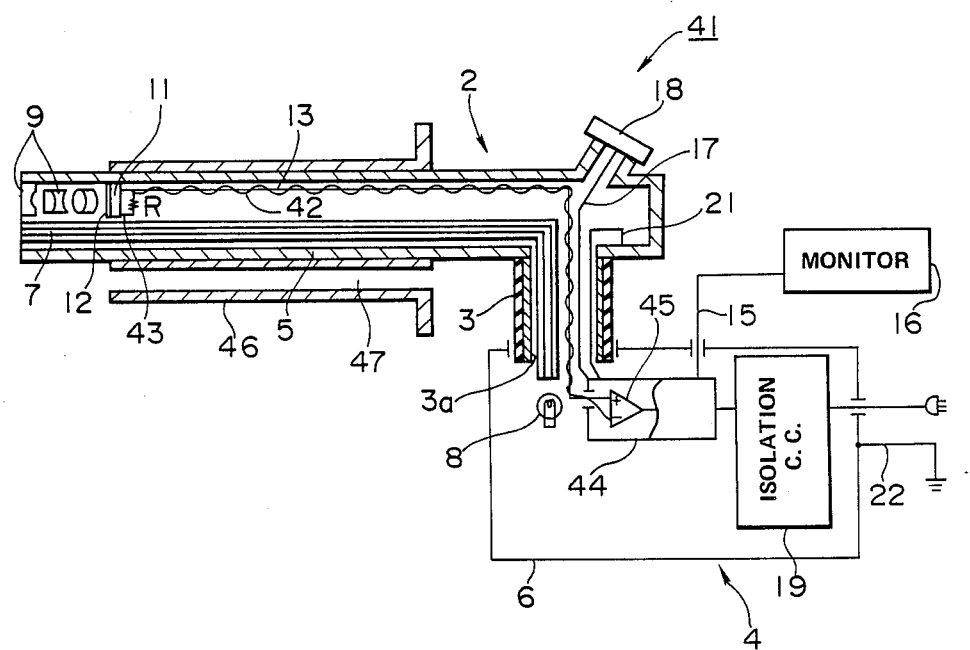
FIG. 3 relates to the third embodiment of the present invention and is a formation view of a rigid electronic endoscope.

FIG. 3 shows the third embodiment of the present invention.

In a rigid electronic endoscope apparatus 41 of this third embodiment, there is used a dummy cable 42 to be a twisted pair twisted together with the signal cable 13 transmitting the picture signal of the CCD. This dummy cable 42 is connected at the end on the CCD 11 side to a GND terminal 43 of the CCD 11 through a resistance R and is led at the end on the base side to the rear step side through a differential amplifier 45 within the video process circuit 44. By the way, the above mentioned GND terminal 43 of the CCD 11 is of the same potential as of the GND terminal of the video process circuit 44.

The above mentioned resistance R is set to be equal to the output impedance of the CCD 11. The signal cable 13 and dummy cable 42 are made a twisted pair so that, in case high frequency noises mix in the reverse phase, they may be canceled with each other. On the other hand, by passing the same phase component through the differential amplifier 45, the high frequency noises are canceled.

By the way, in this embodiment, the jacket tube 46 together with the guide tube part through which the endoscope body 2 is inserted forms a treating tool channel 47 through which the treating tool can be passed.

The other are of the same formation as of the above mentioned first embodiment. The same reference numerals are attached respectively to the same components.

According to this third embodiment, by obtaining the differential output of both cables 13 and 42, the external noises can be more effectively removed, the reduction of S/N can be prevented and the deterioration of the picture quality can be prevented.

By the way, in the above described respective embodiments, the rigid endoscope has been explained. However, the present invention is not limited to it but can be applied the same to a flexible electronic endoscope using a solid state imaging device for the imaging means. In such case, as a conductive sheath member corresponding to the metallic sheath tube 5 in FIG. 1 and having a noise shielding function, such tip forming member as a net tube (blade) or spiral tube (flex) may be used as made electrically conductive. Also, the forceps channel may be formed of such conductive member as a net tube. The above described embodiments may be combined.

Figure 4:
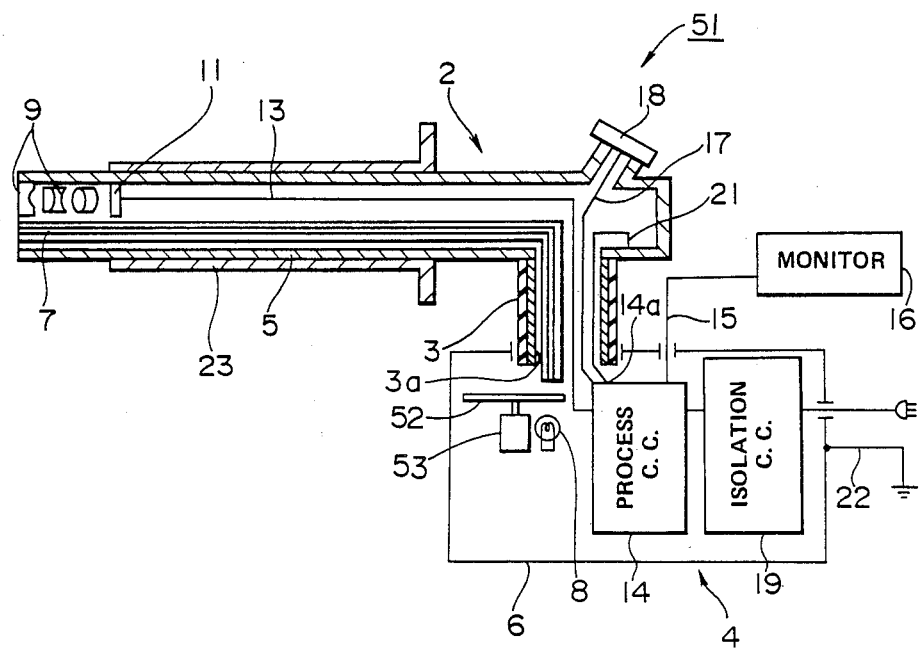

FIG. 4 shows the fourth embodiment of the present invention.

A rigid electronic endoscope 51 of this embodiment is the rigid electronic endoscope 1 of the first embodiment in which the imaging system is made to be of a frame sequential type.

A sheath tube 5 is formed to be like a small diameter cylindrical tube. A light guide 7 formed of a fiber bundle is inserted through this sheath tube 5, is further inserted through a connecting tube 3 and is connected to a control apparatus 4. An illuminating light emitted from a light source lamp 8 and having passed through a plurality of color transmitting filters provided in a rotary filter 52 will enter the entrance end surface of this light guide 7. These plurality of color transmitting filters can respectively transmit color lights, for example, of red, green and blue and can emit red, green and blue color lights when the rotary filter 52 is rotated and driven by a motor 53. An object illuminated by these illuminating lights will be made to form an image on the imaging surface of a CCD 11 by an objective lens system 9. This optical image will be photoelectrically converted by the CCD 11. This photoelectrically converted video signal will be output by the application of a CCD driving signal output from a driving circuit not illustrated, for example, within the control apparatus 4. This video signal will be processed by a process circuit 14 within the control apparatus 4.

The others are of the same formation as of the first embodiment. The same reference numerals are attached to the same members.

In this embodiment, as the imaging system is made to be of a frame sequential type, the imaging surface of the CCD 11 can be made small and the sheath tube 5 can be made smaller in the diameter than in the above mentioned respective embodiments.

As described above, according to the present invention, the signal processing means processing the output video signal of the solid state imaging device is made in a floating state from the earthing of the external power feeding means by the isolation means, the ground of this signal processing means is conducted with the sheath member of the endoscope body and therefore noises can be prevented from mixing into the video signal to reduce S/N.

What is claimed is:

1. A rigid electronic endoscope, comprising:
   an endoscope having an elongated insertable portion which is connected to a front portion of an operating part, a holding part on an end portion of said endoscope, a solid state imaging means for outputting an electrical signal by electrically converting an object image within said insertable portion, and a sheath means of said insertable portion for forming a conductive shielding means;
   a signal processing means connected to said imaging means, for processing said electrical signal obtained by said endoscope, said signal processing means having a first ground terminal means; and
   an external current source means connected to said signal processing means, said external current source means having a second ground terminal means, said shielding means being connected to said second ground terminal means, wherein said first ground terminal means and said second ground terminal means are isolated from each other for preventing high frequency waves on said sheath means from effecting said electrical signal output of said endoscope.

2. A rigid electronic endoscope according to claim 1 wherein said insertable portion is inserted in a jacket tube.

3. A rigid electronic endoscope according to claim 2 wherein said jacket tube is isolated from said shielding means.

4. A rigid electronic endoscope according to claim 1 wherein a dummy cable for removing noises is electrically connected to said solid state imaging means and signal processing means.

* * * * *

UNITED STATES PATENT AND TRADEMARK OFFICE
CERTIFICATE OF CORRECTION

PATENT NO.:     4,879,992
DATED      :    November 14, 1989
INVENTOR(S):    Shinichi NISHIGAKI et al.

It is certified that error appears in the above-identified patent and that said Letters Patent is hereby corrected as shown below:

Claim 1, column 6, line 25, change "second" to --first--.

Signed and Sealed this

Sixteenth Day of September, 1997

Attest:

BRUCE LEHMAN

*Attesting Officer*     *Commissioner of Patents and Trademarks*